United States Patent [19]

Brennan

[11] 4,118,570

[45] Oct. 3, 1978

[54] PROCESS FOR PRODUCING SODIUM DICHLOROISOCYANURATE

[75] Inventor: James P. Brennan, Wallingford, Conn.

[73] Assignee: Olin Corporation, New Haven, Conn.

[21] Appl. No.: 783,241

[22] Filed: Mar. 31, 1977

[51] Int. Cl.$^2$ .................. C07D 251/32; C07D 251/36
[52] U.S. Cl. ...................................... 544/190; 544/192
[58] Field of Search ................................. 544/190, 192

[56] References Cited

U.S. PATENT DOCUMENTS 3,184,458 5/1965 Frazier .................................. 544/190
3,352,860 11/1967 Hass et al. ............................ 544/190

Primary Examiner—John M. Ford
Attorney, Agent, or Firm—William A. Simons; Thomas P. O'Day

[57] ABSTRACT

The present invention is an improvement in a process for the production of sodium dichloroisocyanurate (SDCC) wherein both an aqueous reaction mixture containing SDCC and the by-product $NCl_3$ and a gaseous phase containing $NCl_3$ vapor are formed, said improvement comprising passing an inert gas through said aqueous phase to remove said $NCl_3$ vapor from said gaseous phase.

12 Claims, No Drawings

PROCESS FOR PRODUCING SODIUM DICHLOROISOCYANURATE

BACKGROUND OF THE INVENTION

A. Field of the Invention

The present invention relates to an improvement in a process for making sodium dichloroisocyanurate. In particular, the present invention relates to an improvement in a process for making sodium dichloroisocyanurate wherein a hazardous by-product $NCl_3$ is removed.

B. Description of the Prior Art

Sodium dichloroisocyanurate, hereinafter sometimes called SDCC for the sake of brevity, is widely used today as an important source of active chlorine in solid detergent and bleaching compositions, and in the chlorination of water, especially swimming pools. This compound is desirable for these uses because it remains relatively stable under both ambient storage conditions and in the absence of substantial amounts of moisture. Furthermore, it is very soluble in water and will readily give off active chlorine when placed in an aqueous slurry.

One known process for preparing SDCC is to react together trichloroisocyanuric acid, cyanuric acid and sodium hydroxide in an aqueous solution to form the desired SDCC and $H_2O$. This process is represented by the following equation:

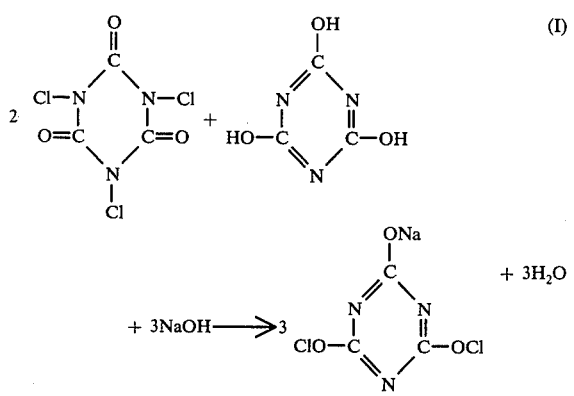

However, in this process several by-products may be formed. The most troublesome of these possible by-products is nitrogen trichloride ($NCl_3$). This compound is a volatile yellow oil which may readily explode in either the liquid or vapor phase when subjected to shock, organic material or temperatures of 60° C. or higher. Therefore, the presence of appreciable amounts of $NCl_3$ in the SDCC reactor may be quite hazardous.

Another known process for producing SDCC is reacting dichloroisocyanuric acid with sodium hydroxide in an aqueous reaction medium as taught in U.S. Pat. No. 3,299,060, issued to Kovalsky et al. on Jan. 17, 1967. Still another is reacting one mole of trisodium isocyanurate with two moles of trichloroisocyanuric acid to produce three moles of SDCC.

In the past, it was necessary to further process the SDCC reaction mixture of the above reactions to remove these undesirable quantities of $NCl_3$. This procedure was time-consuming and costly. Further, it was necessary to shut down the SDCC processes at periodic intervals to remove accumulations of this explosive compound from the reactor and other processing equipment.

Therefore, a need exists in the SDCC industry to find a process improvement to the above reaction which would result in the production of a SDCC reaction mixture that is substantially free of nitrogen trichloride, thereby helping eliminate the need for further processing of the product. Also, such an improvement would be even more beneficial if it also aided in the elimination of the periodic shutdown in the process. It is believed that the present invention solves this need.

U.S. Pat. No. 3,184,458, issued to Frazier on May 18, 1965, discloses the employment of an inert purge gas to remove $NCl_3$ in the production of trichloroisocyanuric acid. However, the process discussed in that patent and the present process are far different because that prior art process employs a specific chlorination reaction whereas the present invention does not chlorinate with gas. Still further, the process taught therein employs an inert purge gas after the reaction is over, thereby requiring separate stripping apparatus, or in combination with the chlorine gas during the reaction.

BREIF SUMMARY OF THE INVENTION

The present invention is an improvement in a process for the production of sodium dichloroisocyanurate (SDCC) wherein both an aqueous reaction mixture containing SDCC and the by-product $NCl_3$ and a gaseous phase containing $NCl_3$ vapor are formed, said improvement comprising passing an inert gas through said gaseous phase to remove said $NCl_3$ vapor from said gaseous phase.

DETAILED DESCRIPTION

The present invention may be employed in any process for making SDCC wherein the undesirable by-product $NCl_3$ is also produced. Specifically, any of the particular reactions cited above may be employed; however, for simplicity of discussion, the following detailed description will be limited to the preferred reaction wherein trichloroisocyanuric acid, cyanuric acid, and sodium hydroxide are reacted. This is represented by Equation (I) above. Yet, it should be understood that all conventional reactions for making SDCC are encompassed by the present invention, wherein $NCl_3$ is formed.

As shown above in the reaction represented by Equation (I), the three reactants are reacted together to form the desired SDCC product and $H_2O$. This reaction is normally carried out in an aqueous solvent and may be employed in any suitable batch or continuous reactor.

The cyanuric acid employed in the present process is preferably of high purity (i.e., about 95% by weight pure or higher). The use of high purity cyanuric acid results in higher yields of SDCC and a purer SDCC reaction mixture. Furthermore, the use of impure commercially available grades of cyanuric acid is usually accompanied by increased amounts of urea, which is a particularly good source for the conversion into the undesired byproduct $NCl_3$.

Likewise, it is desirable to employ highly pure (i.e., 95% by weight pure or higher) trichloroisocyanuric acid for the present process. This compound is commercially available as a solid compound and there are several commercial processes for making it. One such process is illustrated in U.S. Pat. No. 3,184,458, cited above.

For the present invention, for each mole of cyanuric acid being reacted, preferably about 1.5 to about 2.5 moles, more preferably about 1.8 to about 2.2 moles, and most preferably about 1.95 to about 2.05 moles of trichloroisocyanuric acid are employed. Moreover, it should be noted that the use of a molar ratio of trichloroisocyanuric acid to cyanuric acid below the ratio of about 2:1 will increase the chances that unreacted cyanuric acid will be left in the reaction mixture, which may contribute unacceptable impurities besides $NCl_3$. Further, the use of a molar ratio of trichloroisocyanuric acid to cyanuric acid above the ratio of about 2:1 may result in trichloroisocyanuric acid being left in the reaction mixture, which may cause an excess of active chlorine available in the reaction mixture. This, in turn, will probably result in the formation of large amounts of $NCl_3$.

Sodium hydroxide for the present reaction may be in either a solid form or in an aqueous solution of any available concentration. Preferably, it is employed in an aqueous solution because then addition to the reactor is easier. A commercially available aqueous solution containing 50% by weight NaOH is preferred.

For the present invention, for each mole of cyanuric acid being reacted, it is preferable to react from about 2.5 to about 3.5 moles, more preferably from about 2.8 to 3.2 moles, and most preferably from about 2.95 to 3.05 moles, of sodium hydroxide. It should be understood that use of a molar ratio of sodium hydroxide to cyanuric acid below the ratio of about 3:1 will leave a reaction mixture with unreacted cyanuric acid and chloroisocyanurates, again leaving a considerable amount of undesired impurities. Also, the use of molar ratio of sodium hydroxide to cyanuric acid above the ratio of about 3:1 will result in a reaction mixture having too high a pH, which may cause the SDCC product to decompose and more $NCl_3$ may be formed.

Water is normally employed as a solvent for the reaction. It may be mixed with any of the reactants before addition into the reactor or may be added to the reactor before the reactants are added. The amount of water used is not critical to the present invention, but it is preferable to employ sufficient water so that the reaction mixture will have a total solids contents from about 25% by weight to 50% by weight.

According to the process improvement of the present invention, an inert gas or a mixture of inert gases is passed through the gaseous phase which is above the aqueous reaction mixture to remove $NCl_3$ vapor from the gaseous phase. The inert gas can be either directly introduced into the gaseous phase or first introduced into the aqueous reaction mixture, and then passed upward through the gaseous phase. Normally, the aqueous reaction mixture will be from about 20% to about 80% of the reactor volume with the gaseous phase constituting the gas void of the reactor above the aqueous reaction mixture. Of course, the volume of the aqueous reaction mixture in the reactor may be outside this range of percentages, depending on reactor design and other considerations.

The inert gas may be air, nitrogen, carbon dioxide, helium or any other suitable gas or mixture of gases that is inert to the other reaction constituents present. Air and nitrogen are preferred because of their easy availability. The inert gas may be introduced into the gaseous phase by means of a sparge tube or tubes. More than one point of introduction may be employed. After passing through the gaseous phase, the inert gas, now carrying $NCl_3$ vapor and other gaseous impurities, may vent from the gaseous phase at a location or locations remote from the introduction point or points. These introduction and venting points should be selected so that effective sweeping of the gaseous phase by the inert gas will occur. After venting, the vented gases may, if desired, be scrubbed with a suitable scrubber apparatus. The scrubbed gases then can be released to the atmosphere or recycled back into the reactor or employed in other chemical processes.

The amount of inert gas passed through the gaseous phase will depend chiefly on the $NCl_3$ content in that phase and in the aqueous reaction mixture and the desired amount of $NCl_3$ to be removed. The explosive concentrations of $NCl_3$ in the liquid state are those which exceed its solubility in water. Normally, this is around 2000 parts per million parts of $H_2O$. Above this concentration, $NCl_3$ forms a volatile yellow oil which may easily explode under the right conditions such as shock, organic impurities being present or high temperatures. Because this oil is volatile, a vapor of $NCl_3$ is simultaneously formed which may be present in either the aqueous reaction mixture or the gaseous phase above the aqueous reaction mixture. When the concentration of the $NCl_3$ vapor in the gaseous phase reaches about 5% to 6% by volume, the $NCl_3$ present therein may explode for the same reasons as the liquid $NCl_3$. It should be understood that these liquid and vapor states of the $NCl_3$ are in equilibrium and removal of the $NCl_3$ vapor will reduce the $NCl_3$ concentration of the liquid state. Therefore, it is preferred to pass at least about 0.05 volumes of inert gas per minute through the gaseous phase. More preferably, from about 0.1 to about 3.0 volumes, most preferably from about 0.2 to about 0.4 volumes per minute, of inert gas may be passed through the gaseous phase to give satisfactory removal of the $NCl_3$ vapor formed therein. One (1.0) volume of inert gas is defined to be the same as the volume of aqueous reaction mixture in the reactor. Passing the inert gas at a rate above about 3.0 volumes normally will not further reduce the $NCl_3$ concentration in the gas phase. Also, while in some cases rates below 0.05 volumes/minute may be suitable, rates above this should usually be employed to insure adequate removal and prevent the formation of explosive $NCl_3$ concentrations in both the gas and liquid phases.

The sparge tube inlet or inlets may be located either above or below the top surface of the aqueous reaction mixture. Preferably, these inlets are placed below the top surface of the aqueous reaction mixture so that the inert gas is introduced under the surface. This results in the removal of $NCl_3$ vapor from the liquid phase as well as the gas phase. Therefore, it is possible that more $NCl_3$ may be removed from the gaseous phase and reaction mixture and the final SDCC product may contain less amounts of $NCl_3$. Furthermore, sub-surface introduction of the inert gas will keep the reaction mixture agitated and aid in preventing the build-up of potentially explosive $NCl_3$ oil droplets in the liquid reaction mixture. While mechanical agitation is normally used for this reason, this sub-surface sparging with an inert gas provides an acceptable back-up system for agitating the reaction mixture and thus gives the process an added degree of safety.

In carrying out the present process, an exothermic heat of reaction is given off, thereby raising the temperature of the aqueous reaction mixture. Therefore, to prevent too high temperatures and the increased chance of product decomposition and $NCl_3$ explosion, it is normally desirable to keep the reaction mixture cooled by some means. This can be accomplished by employing pre-cooled reactants or conventional reactor cooling systems such as heat exchangers, ice-water baths and refrigerants. Preferably, the reaction temperatures are kept in the range of about −5° C. to about 60° C., more preferably from about 15° C. to about 50° C.

The reaction is usually carried out at substantially atmospheric pressures. Reduced pressures may also be employed to aid in removing the $NCl_3$ gas. However, pressures substantially above atmospheric pressure are not usually desirable. Increased pressures may cause the $NCl_3$ to have increased solubility in the aqueous reaction mixture, thereby possibly reducing the formation of $NCl_3$ vapor. This can lead to aqueous reaction mixture having dangerously high concentrations of $NCl_3$ therein which may explode if the pressure is reduced. Furthermore, less amounts of $NCl_3$ vapor can be removed under such conditions.

Other conventional reaction conditions which are conventionally used in SDCC production may be employed. For example, in a batch reaction, the three reactants may be charged into a batch reactor, either simultaneously or one after another, after or in aqueous solvents. The reaction is usually allowed to proceed at the desired temperatures and pressures over a period of from about 0.25 to 6.0 hours, depending on the volume of ingredients used. In a continuous operation, the reactants may be pumped or dropped while in either aqueous solution or solid form into a continuous reactor, which can have a reaction zone volume such as to provide a residence time of from about 0.25 to about 4.0 hours, again depending upon the production capacity desired.

After the reaction is complete, the liquid reaction mixture (i.e., aqueous slurry) containing the desired solid SDCC product and possibly some $NCl_3$ and residues of unreacted starting materials is filtered or centrifuged to remove the liquid mother liquor. The solids containing the SDCC product are washed and then either dried partially or totally to form either anhydrous SDCC, monohydrate SDCC, dihydrate SDCC or mixtures thereof. This drying can be accomplished by means of either conventionally flash drying or other conventional drying techniques. It should be understood that the steps after the completion of the reaction are not critical to the present invention and any conventional recovery methods can be employed.

The following examples are provided to further illustrate the invention. All parts and percentages are by weight unless otherwise specified.

EXAMPLE I

Sodium dichloroisocyanurate (SDCC) was prepared by the simultaneous addition of trichloroisocyanuric acid, cyanuric acid, and sodium hydroxide into a 500 ml glass vessel having three liquid inlet tubes, one gas inlet tube, stirrer, pH probe, thermometer, gas vent, and one liquid outlet. All three reactants were in the form of aqueous slurries or solutions and were metered into the glass vessel by means of peristaltic pumps. 200 ml of the aqueous trichloroisocyanuric acid slurry was prepared by diluting 108 grams of the reactant with water. Likewise, 200 ml of the aqueous cyanuric acid slurry was prepared by dilution of 30 grams of the reactant with water. A commercial 50% by weight aqueous solution of NaOH was also employed. The trichloroisocyanuric acid was metered into the vessel at a rate of 7.8 millimoles per minute. The cyanuric acid was metered in at 3.9 millimoles per minute. And the NaOH was added at a rate of 11.7 millimoles per minute. The pH of the reaction was maintained at about 6.5. The average liquid volume in the reactor was held at about 200 ml by removing the reaction mixture through the liquid outlet tube by means of another pump. The average residence time for the reaction mixture was about 30 minutes. The temperature of the vessel was about 40° C.

As soon as 200 ml of reactants were admitted to the vessel, nitrogen gas was pumped into vessel under the surface of the liquid reaction mixture while the reaction mixture was stirred. The rate of the $N_2$ purge was 75 ml/minute or 0.375 volumes per minute. The concentration of $NCl_3$ in the vent gas was measured and found to be about 1.6% by volume, which is well below the known explosive concentration of about 5% to 6% by volume $NCl_3$.

A similar system without the gas purge could generate $NCl_3$ in amounts that would exceed the solubility in water (approximately 2000 parts per million parts of water) thereby forming both a separate liquid phase which can easily detonate and a vapor phase which could reach concentrations over about 5% to 6% by volume and also become potentially explosive.

EXAMPLE II

The procedure of Example I was essentially repeated except that the $N_2$ purge rate was varied throughout the reaction. The following data was obtained by measuring the $NCl_3$ concentration in the outlet gases as a function of the $N_2$ purge rate:

| $N_2$ Purge Rate (ml./min.) | Volume of $N_2$ per minute | $NCl_3$ Concentration in Exit Gas |
| --- | --- | --- |
| 40 | .2 | 1.6% by volume |
| 265 | 1.3 | 0.45% by volume |
| 445 | 2.2 | 0.25% by volume |

The volume of $N_2$ was based on an average reaction mixture volume of 200 ml. It can be seen that under these reaction conditions, the above $N_2$ purge rates will keep the $NCl_3$ concentrations well below the potentially explosive concentrations of about 5% to 6% by volume or higher.

EXAMPLE III

Employing essentially the same procedure as in Example I, the gas inlet tube or sparge tube was placed first above the surface of the liquid reaction mixture and $N_2$ was introduced to remove $NCl_3$. After the composition of the vent gas reached equilibrium during the reaction, the sparge tube was relocated at a point below the surface of the liquid reaction mixture. The $N_2$ purge rate and $NCl_3$ concentration in the exit gas were measured in both instances and the following data was obtained:

| Sparge | $NCl_3$ Concentration |
| --- | --- |
| Above surface, 75 ml/min. (.375 volumes $N_2$) equilibrium | 0.8% by volume |
| Sub-surface, 75 ml/min. (.375 volumes $N_2$) initial | 1.1% by volume |
| equilibrium | 0.9% by volume |

As can be noted from the above data, above-surface sparging will remove some $NCl_3$ vapor from above the aqueous reaction mixture. And, this removal of $NCl_3$ will aid in preventing the formation of separate $NCl_3$ liquid phase in the reaction mixture. However, nonformation of the NCl₃ liquid phase is more dependent on adequate agitation of reaction mixture, such as by mechanical stirring means. Therefore, above-surface sparging could be hazardous in the event of mechanical failure. Sub-surface sparging with inert gas will agitate the reaction mixture in addition to that provided by the stirrer and, thus, provides an added degree of safety to the process.

What is claimed is:

1. In a process for the production of sodium dichloroisocyanurate wherein trichloroisocyanurate, cyanuric acid and sodium hydroxide are reacted together in an aqueous solution to form an aqueous reaction mixture containing sodium dichloroisocyanurate and the by-product nitrogen trichloride and a gaseous phase containing the by-product nitrogen trichloride vapor; the improvement which comprises:

purging said nitrogen trichloride vapor from said gaseous phase by passing an inert gas through said gaseous phase during said reaction.

2. The process of claim 1 wherein said inert gas is introduced under the liquid surface of said aqueous reaction mixture and then passed through said gaseous phase.

3. The process of claim 1 wherein said inert gas is nitrogen.

4. The process of claim 1 wherein said inert gas is air.

5. The process of claim 1 wherein said inert gas is passed through said gaseous phase at a rate of at least about 0.05 volumes/minute per volume of said aqueous reaction mixture.

6. The process of claim 1 wherein about 1.5 to about 2.5 moles of trichloroisocyanuric acid are reacted per each mole of cyanuric acid employed.

7. The process of claim 6 wherein about 2.5 to about 3.5 moles of sodium hydroxide are employed per mole of cyanuric acid employed.

8. The process of claim 7 wherein sufficient water is present in order that said aqueous reaction mixture will have a total solids content of from about 25% by weight to about 50% by weight.

9. The process of claim 8 wherein said inert gas is introduced under the liquid surface of said aqueous reaction mixture and then passed through said gaseous phase.

10. The process of claim 9 wherein said inert gas is selected from the group consisting of air and nitrogen.

11. The process of claim 10 wherein said inert gas is passed through said gaseous phase at a rate of from about 0.2 to about 0.4 volumes/minute per volume of said aqueous reaction mixture.

12. The process of claim 11 wherein about 1.95 to about 2.05 moles of trichloroisocyanuric acid are employed per each mole of cyanuric acid employed and about 2.95 to about 3.05 moles of sodium hydroxide are employed per each mole of cyanuric acid employed.

* * * * *